(12) United States Patent
Butts et al.

(10) Patent No.: US 6,387,101 B1
(45) Date of Patent: *May 14, 2002

(54) DEFORMABLE INTRAOCULAR LENS INJECTING APPARATUS AND METHOD

(75) Inventors: Maurice D. Butts, Fullerton; Thomas J. Chambers, Upland; Flora Wang, Monterey Park; Robert S. Friedman, Los Angeles, all of CA (US)

(73) Assignee: STAAR Surgical Company, Inc., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/516,767

(22) Filed: Mar. 1, 2000

Related U.S. Application Data

(63) Continuation-in-part of application No. 09/422,984, filed on Oct. 22, 1999, now Pat. No. 6,312,433.

(51) Int. Cl.[7] ................................................. A61F 9/007
(52) U.S. Cl. ..................................................... 606/107
(58) Field of Search ........................ 606/107; 623/6.12, 623/907; 604/220

(56) References Cited

U.S. PATENT DOCUMENTS

| 4,681,102 A | * | 7/1987 | Bartell ...................... 623/6.12 |
| 4,834,094 A | * | 5/1989 | Patton et al. ................ 606/107 |
| 5,499,987 A | * | 3/1996 | Feingold ..................... 606/107 |
| 5,947,975 A | * | 9/1999 | Kikuchi et al. .............. 606/107 |

* cited by examiner

Primary Examiner—Eduardo C. Robert
(74) Attorney, Agent, or Firm—William L. Kim; Law Offices of William L. Klima, P.C.

(57) ABSTRACT

A deformable intraocular lens injecting apparatus for inserting a deformable intraocular lens through a small incision into an eye. The apparatus includes a lens injecting body including a lens receiver configured to be operated between an open configuration and a closed configuration, and a nozzle portion provided with a tip portion configured to be inserted through a small incision into an eye. The nozzle portion is configured for connection to the lens receiver of the lens injecting body, and the nozzle portion and the lens receiver defining a lens delivery passageway. A plunger is slidably disposed relative to the lens delivery passageway and configured to engage a deformable intraocular lens within the lens delivery passageway of the lens receiver, and to move the deformable intraocular lens out of the lens delivery passageway into the eye.

20 Claims, 12 Drawing Sheets

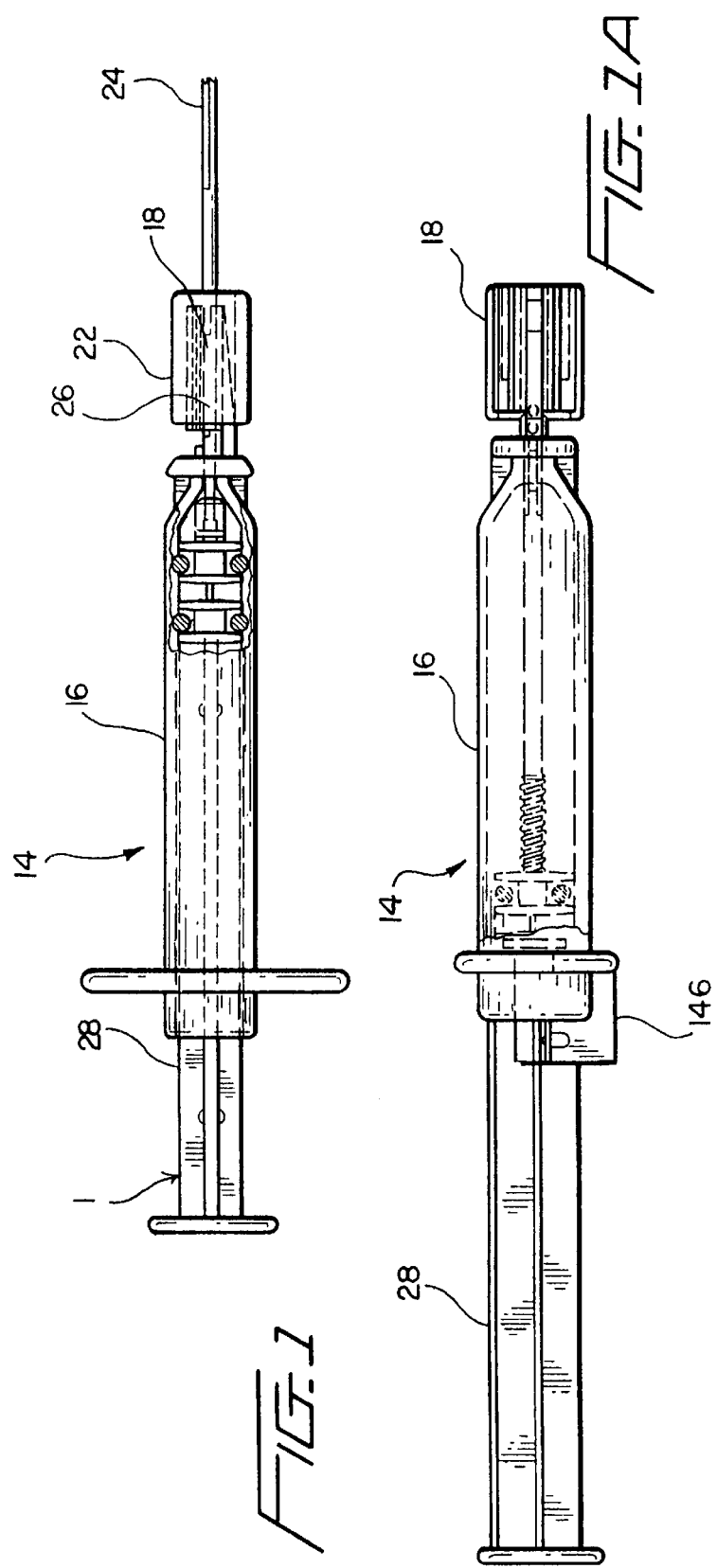

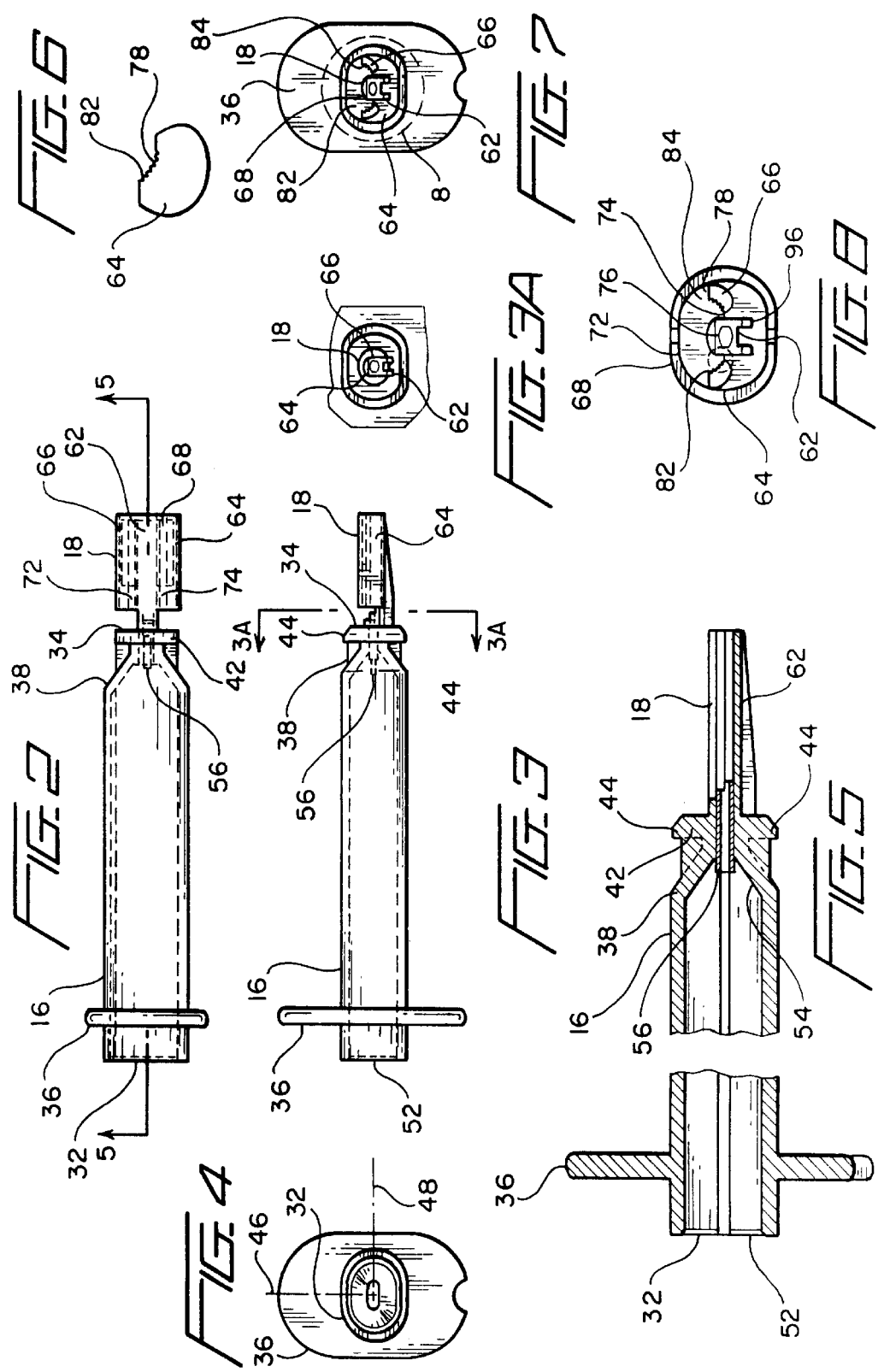

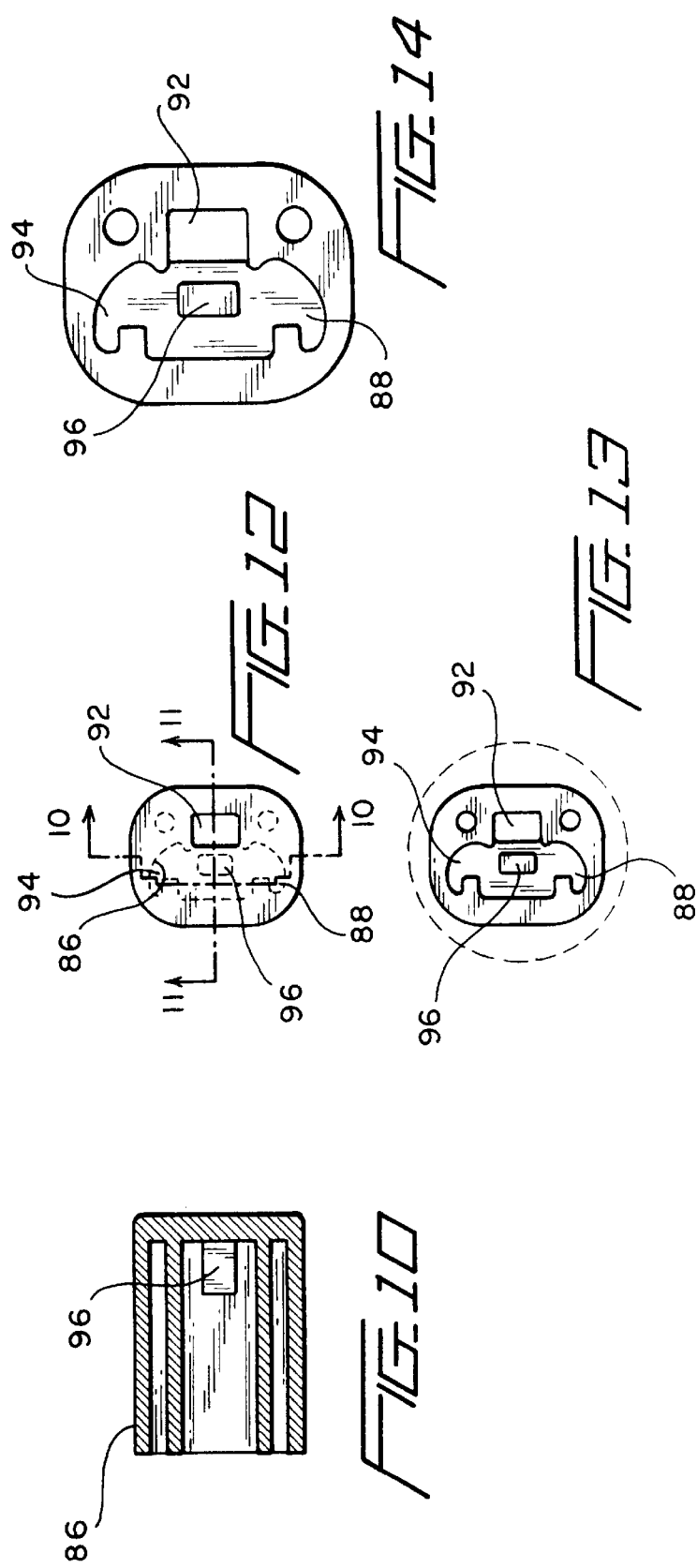

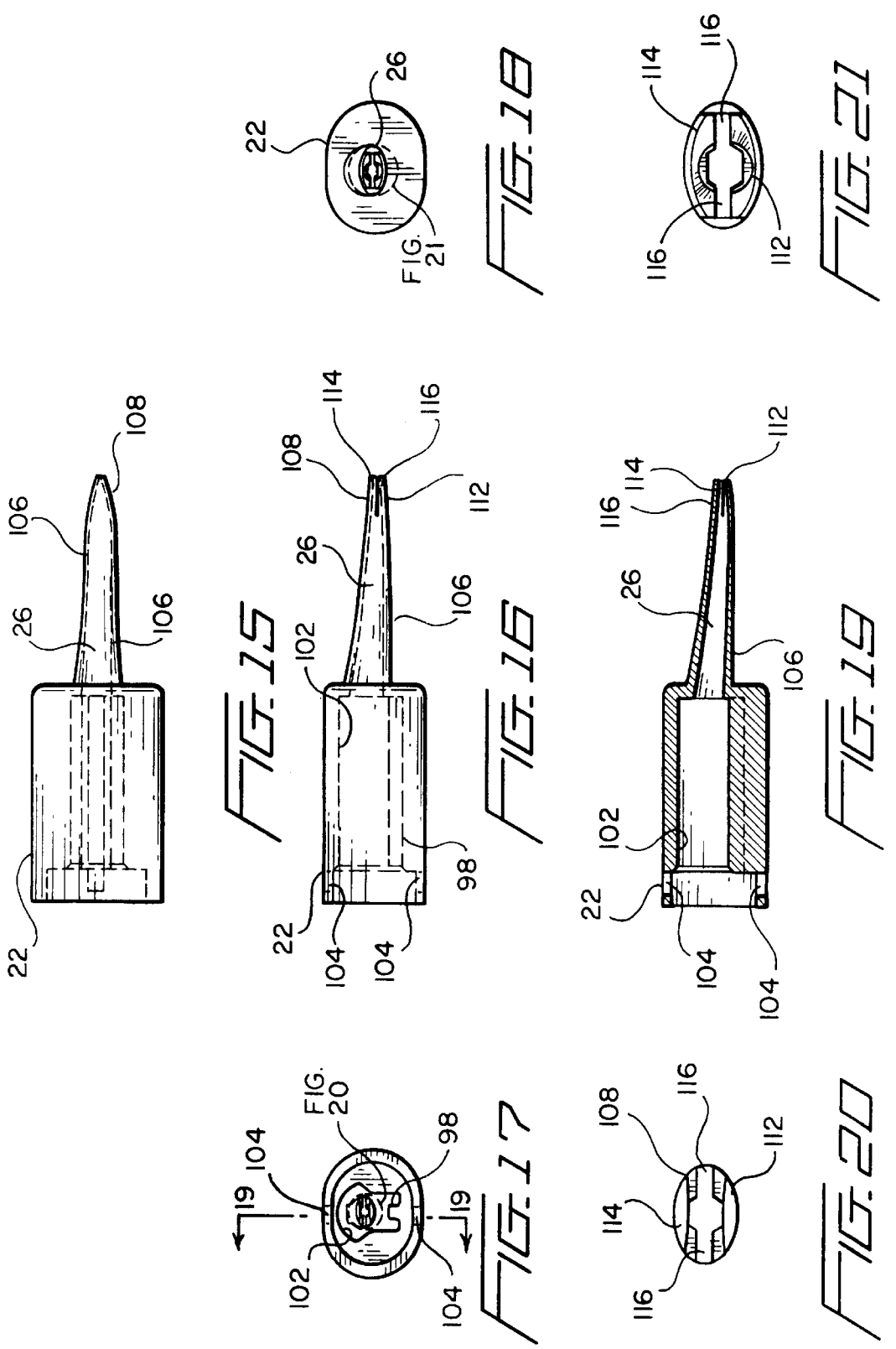

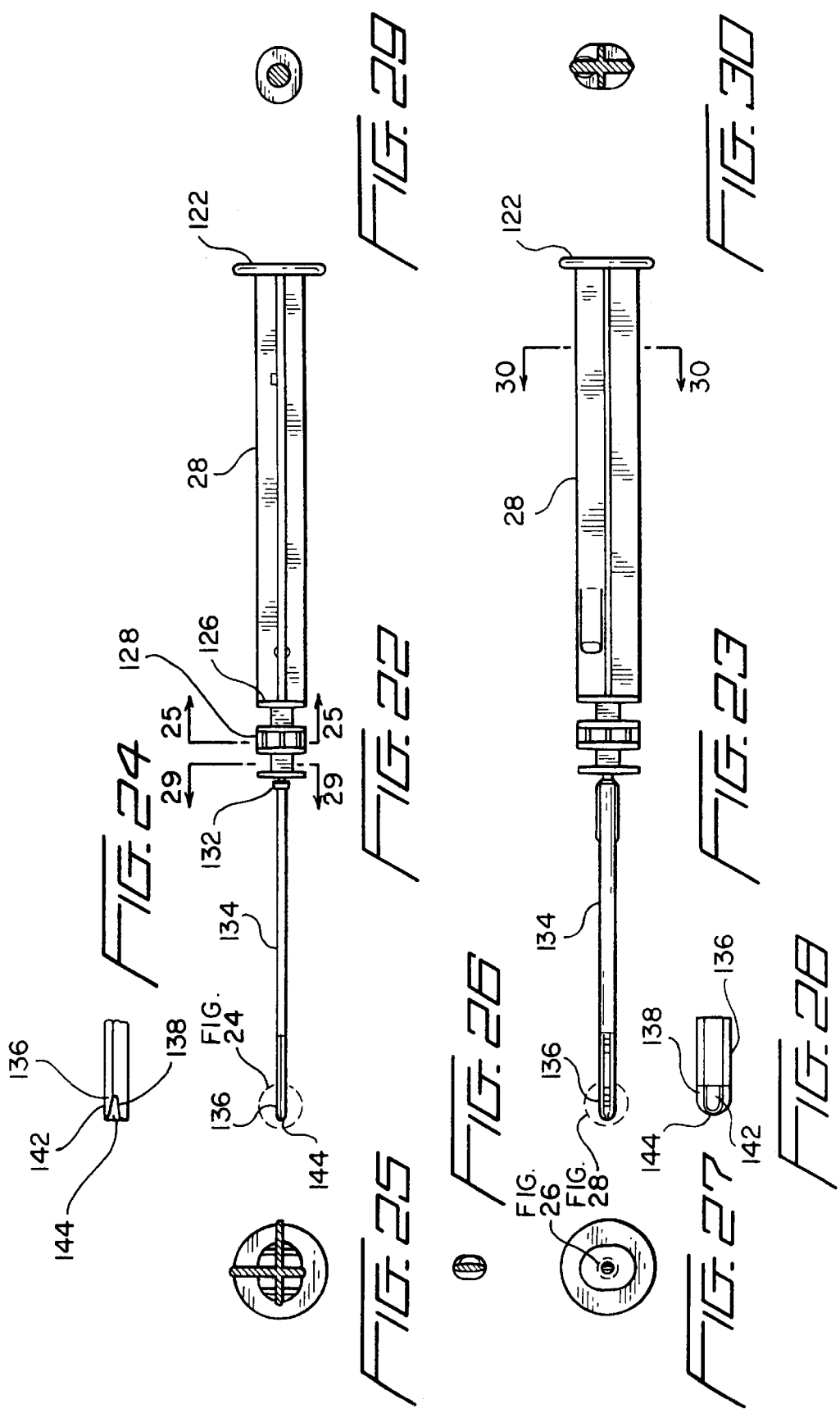

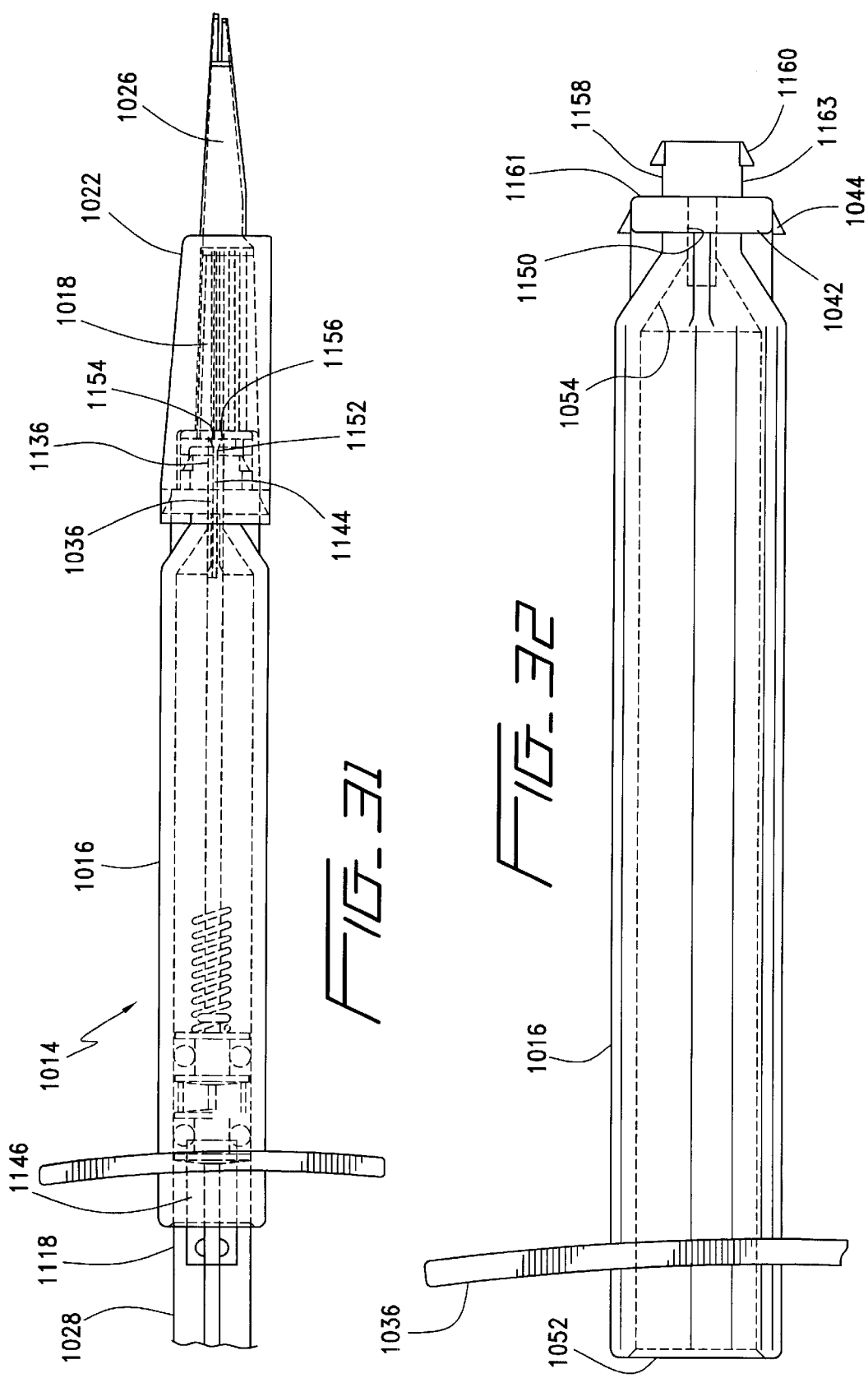

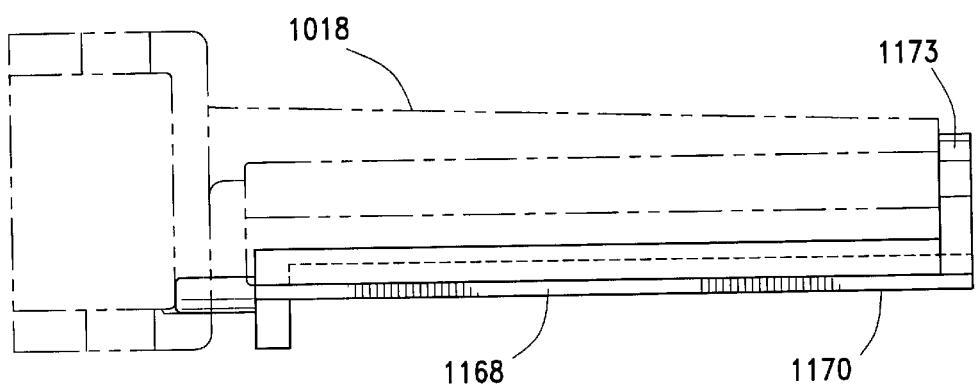
FIG_38
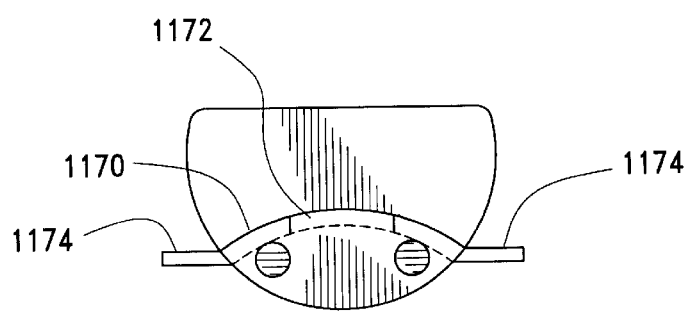
FIG_39
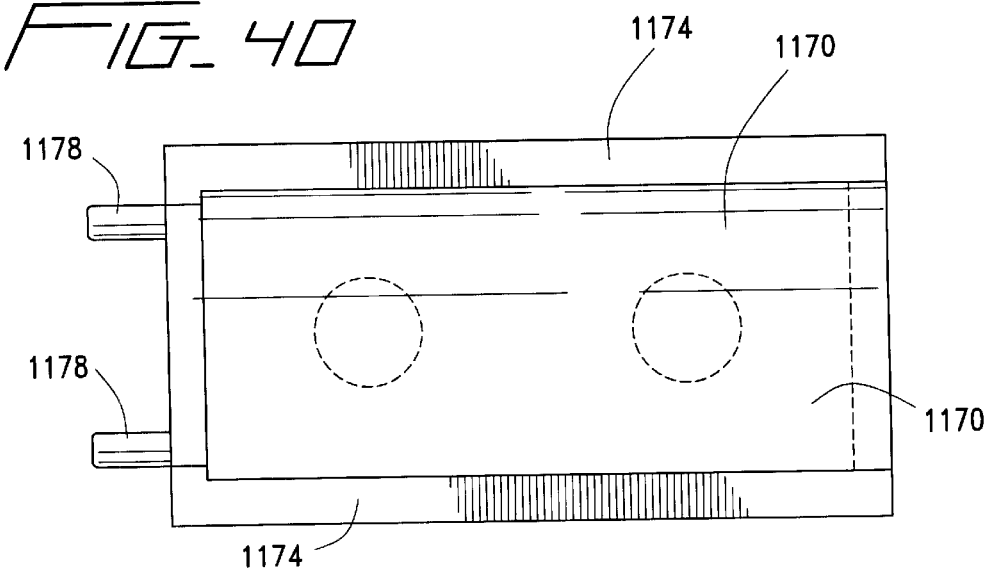
FIG_40

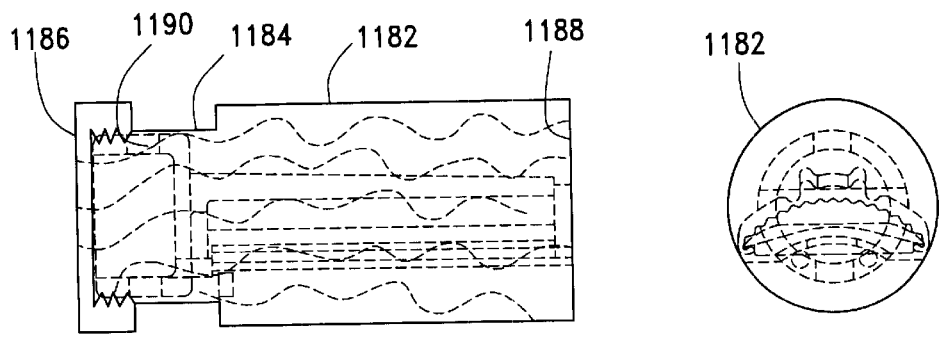
FIG_41  FIG_42
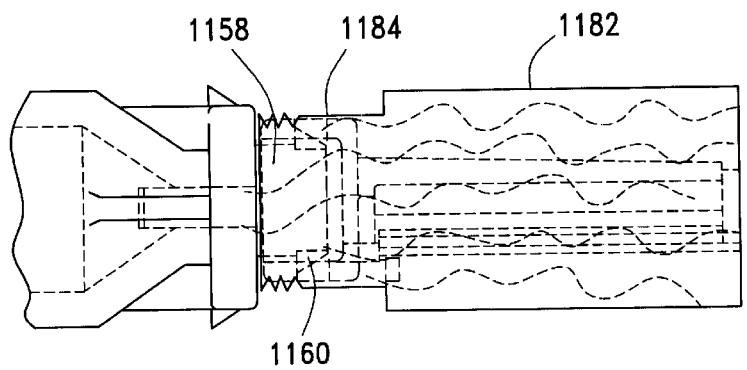
FIG_43
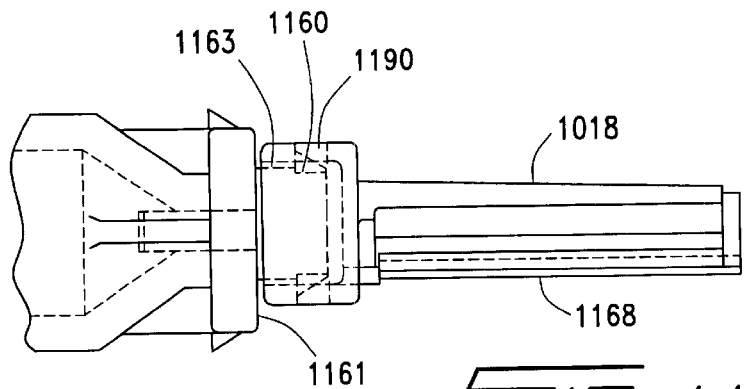
FIG_44
FIG_45 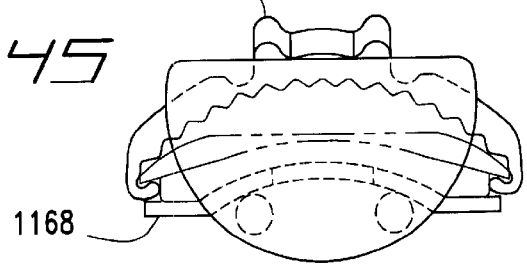

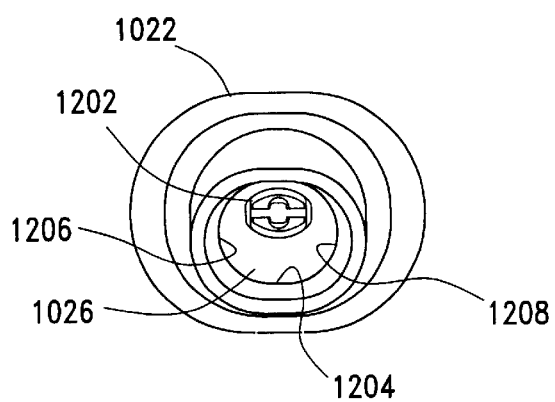
FIG_49
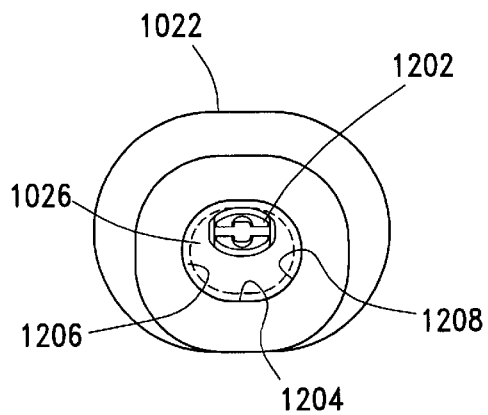
FIG_50
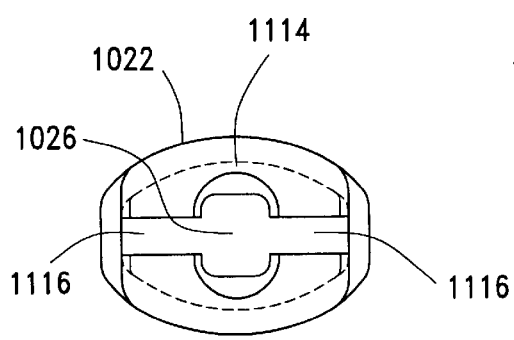
FIG_51
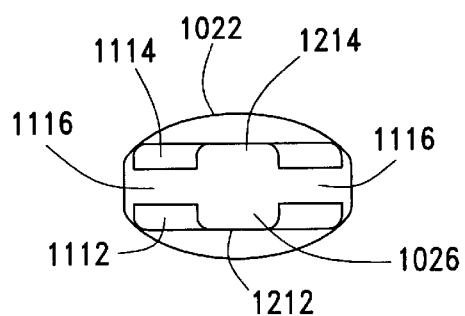
FIG_52

DEFORMABLE INTRAOCULAR LENS INJECTING APPARATUS AND METHOD

RELATED APPLICATION

This is a continuation-in-part application of U.S. Patent Application entitled "Deformable Intraocular Lens Injecting Apparatus and Method", U.S. patent application Ser. No. 09/422984, filed on Oct. 22, 1999, fully incorporated by reference herein, now U.S. Pat. No. 6,312,433.

FIELD OF THE INVENTION

The present invention relates to the introduction of an artificial lens to an eye. More specifically, the present invention relates to an apparatus and method for implanting a deformable intraocular lens into an eye.

BACKGROUND OF THE INVENTION

The use of deformable intraocular lenses in the treatment of cataracts and other refractive problems has become commonplace. There are many devices and methods currently in use for the delivery of a deformable intraocular lens into the eye. Complications continue to arise out of the use of these devices and methods, specifically, damage to the ocular tissues and/or damage to the implanted deformable intraocular lens. There is a need for an apparatus and method for delivering a deformable intraocular lens to the eye which does not damage the ocular tissue or the implanted lens.

SUMMARY OF THE INVENTION

It is a first object of the present invention to provide an apparatus and method for introducing a deformable intraocular lens to the eye.

It is a second object of the present invention to provide an improved apparatus and method for introducing a deformable intraocular lens to the eye.

It is a third object of the present invention to provide an apparatus which deforms a deformable intraocular lens for introduction through a small ocular incision to the eye.

It is a fourth object of the present invention to provide an apparatus which moves a deformed intraocular lens into the eye.

It is a fifth object of the present invention to provide an apparatus which allows a deformed intraocular lens to release stored energy associated with the lens deformation process in a controlled manner.

It is a sixth object of the present invention to provide an apparatus which provides at least one tool for manipulating a lens within the eye.

It is a seventh object of the present invention to provide an apparatus which may be pre-loaded with a deformable intraocular lens.

It is an eighth object of the present invention to provide an apparatus which may be pre-loaded with a deformable intraocular lens in a non-deformed condition.

It is a ninth object of the present invention to reduce the potential for introduction of user error into the process for the delivery of a deformable intraocular lens to the eye.

It is a tenth object of the present invention to further automate the process for delivering a deformable intraocular lens to the eye.

It is an eleventh object of the present invention to provide an apparatus which allows a surgeon to view a deformed intraocular lens for determining whether the deformation of the lens is correct for delivery of the lens to the eye.

It is a twelfth object of the present invention to provide an apparatus which allows a surgeon to deform a deformable intraocular lens in preparation for delivery of the lens to the eye without the use of forceps.

It is a thirteenth object of the present invention to provide a deformable intraocular lens injecting apparatus including a lens injecting body including a lens receiver configured to be operated between an open configuration and a closed configuration, a nozzle portion provided with a tip portion configured to be inserted through a small incision into an eye, the nozzle portion configured for connection to the lens receiver of the lens injecting body, the nozzle portion and the lens receiver defining a lens delivery passageway, and a plunger slidably disposed relative to the lens delivery passageway and configured to engage a deformable intraocular lens within the lens delivery passageway of the lens receiver and to move the deformable intraocular lens out of the lens delivery passageway into the eye.

It is a fourteenth object of the present invention to provide a deformable lens injecting apparatus which stores a lens in a slightly vaulted configuration.

It is a fifteenth object of the present invention to provide a deformable intraocular lens injecting apparatus which deforms a lens in preparation for injection of the lens into the eye by greatly decreasing a radius of curvature introduced to the lens during loading of the lens into the apparatus.

It is a sixteenth object of the present invention to provide a deformable intraocular lens injecting apparatus having a lens receiver which stores the lens in a substantially non-deformed state and which deforms the lens in preparation for injection of the lens to the eye.

It is a seventeenth object of the present invention to provide a deformable lens injecting apparatus having a separate lens receiver.

It is an eighteenth object of the present invention to provide a deformable intraocular lens injecting apparatus having a deformable intraocular lens pre-loaded in a component of the apparatus in a hydrating environment.

It is a twentieth object of the present invention to provide a deformable intraocular lens injecting apparatus having a lens receiver provided with a pre-loaded lens and stored in a hydrating environment and further configured for connection to the apparatus within the hydrating environment.

The present invention provides an apparatus and method for inserting a deformable intraocular lens through a small incision into an eye. In a preferred embodiment the apparatus includes a lens injecting body including a lens receiver configured to be operated between an open configuration and a closed configuration, a nozzle portion provided with a tip portion configured to be inserted through a small incision into an eye, the nozzle portion configured for connection to the lens receiver of the lens injecting body, the nozzle portion and the lens receiver defining a lens delivery passageway; and, a plunger slidably disposed relative to the lens delivery passageway and configured to engage a deformable intraocular lens within the lens delivery passageway of the lens receiver, and to move the deformable intraocular lens out of the lens delivery passageway into the eye.

The present invention provides an apparatus which stores, deforms, and delivers a deformable intraocular lens to the eye.

In a preferred embodiment, the apparatus of the present invention is provided to surgical personnel as a package of separate components, each of which is further discussed below, which are assembled by surgical personnel for use.

A lens injecting body and plunger assembly define a component of the apparatus. A lens receiver which connects to the lens injecting body is provided separately from the lens injecting body and plunger assembly. The lens receiver is preferably provided with a pre-loaded deformable intraocular lens. A nozzle is also provided separately from the lens injecting body. Prior to use of the apparatus, the lens receiver is connected to the lens injecting body and plunger assembly and then the nozzle portion is connected to the lens injecting body and plunger assembly.

Through the use of separate components, the apparatus of the present invention provides a lens injecting body and plunger assembly to which a case specific lens receiver and/or case specific nozzle portion may be connected. In other words, surgical personnel need only become proficient in the use of a single lens injecting apparatus to treat a wide variety of patients according to the present invention.

The lens injecting body of the present invention is configured to provide a base or frame to which the other components of the apparatus are connected and also to provide a defined surface which is specifically configured to be easily hand held and manipulated by surgical personnel. Preferably, a lens injecting body is defined by an elongated, rigid, hollow body having a proximal portion including a finger rest for syringe type use of the apparatus and a distal end having first and second sets of tabs specifically configured to engage holes in a lens receiver and nozzle portion, respectively, according to the present invention.

A plunger according to the present invention is preferably provided with the lens injecting body. The plunger is moved relative to the lens injecting body to propagate a lens through a lens delivery passageway defined by the apparatus into the eye. The plunger is preferably further configured to allow surgical personnel to manipulate a lens within the eye.

Another major component of a preferred embodiment of an apparatus according to the present invention is the lens receiver. The lens receiver preferably provides a preloaded deformable intraocular lens, stores the pre-loaded lens in a substantially nondeformed configuration, deforms the lens according to a process for preparing the lens for injection, stores the lens temporarily in a substantially deformed configuration just prior to injection of the lens into an eye, and defines a portion of a lens delivery passageway through and out of which the lens is moved by the plunger of the apparatus into the eye.

A preferred embodiment of a lens receiver includes an elongated base portion and a pair of extending portions which hinge on either longitudinal side of the base portion for operating of the lens receiver between an open configuration and a closed configuration. In an open configuration, interior surfaces of the base portion and extending portions of the lens receiver define a platform which is configured to provide a substantial loading platform for accepting a deformable intraocular lens in a non-deformed configuration. Pre-loading of the lens, typically an optic portion surrounded by haptic portions, includes orienting the lens on the platform of the open lens receiver such that the optic portion is received in a recessed or tray portion of the base portion. Pre-loading also involves engaging each haptic portion of the lens within edge gripping portions of the extending portions. The lens is thereby fixated and predisposed to deformation necessary for delivery of the lens through a small ocular incision.

The lens receiver is further preferably provided with a removable shield portion which is configured to engage the pre-loaded lens receiver in an open configuration. The shield portion protects the lens in the lens receiver during storage and connection of the lens receiver to the lens injecting body. The shield portion also prevents the plunger tip from moving into the lens receiver when the lens receiver is connected to the lens injecting body.

A pre-loaded lens receiver according to the present invention is preferably stored in a sealed storage container of hydrating solution for preserving the lens during storage and delivery of the apparatus to surgical personnel. The hydrating solution may also be provided with a biocompatible lubricant for facilitating delivery of the lens to the eye from the apparatus. Prior to use, a seal is removed from the top of the container which preferably defines a port for receiving the distal end of the lens injecting body. The distal end of the lens injecting body is further configured to engage the proximal end of the lens receiver and to connect thereto by a snap fit connection. The connection occurs conveniently within the storage container. Once connected together, the lens injecting body and lens receiver are removed from the container. The shield portion is then removed from the lens receiver allowing the stored lens to be visually inspected and treated with biocompatible lubricant by surgical personnel.

The platform of the lens receiver is preferably provided with longitudinal ridges which facilitate dispersion of lubricant around the lens and minimize contact between the lens and lens receiver. Deformation of the lens is accomplished by the simple operation of the lens receiver from an open to a closed configuration. Specifically, each extending portion of the lens receiver is grasped simultaneously, preferably, by the thumb and forefinger, and hinged relative to the base portion. During operation of the lens receiver to a closed configuration, a slight radius of curvature introduced to the lens during pre-loading is greatly decreased thereby causing the haptic portions of the lens to curl inwardly and ultimately to slightly overlap within the lens receiver in a "rolled" configuration. Each outer longitudinal edge of the lens receiver may be provided with cooperating locking structure. When the extending portions come together, these edges may interlock to complete the operation of the lens receiver from an open configuration to a closed configuration.

The apparatus of the present invention further includes a nozzle portion which provides a lens delivery passageway through which the deformed intraocular lens is delivered from the lens delivery passageway of the lens receiver to the intraocular implant site. The nozzle portion also serves to secure the lens receiver in a closed configuration and may also be used to manipulate the lens within the eye after ejection therefrom.

The preferred nozzle portion includes a base portion having a proximal end configured to connect to a distal portion of the lens injecting body. The nozzle portion also includes an extending portion and a tip portion which are configured to be introduced to the interior of the eye through a small ocular incision. Preferably, the extending portion is substantially transparent to allow surgical personnel to visually inspect a lens being pushed therethrough.

The nozzle tip portion is provided with a pair of slots which define first and second tip portions. First and second tip portions yield outwardly slightly under the force of a deformable intraocular lens being advanced therethrough and thus function to release elastic energy stored in the deformed lens prior to the complete release of the lens from the lens delivery passageway. First and second tip portions are also shaped differently and may be used to influence the speed and angle at which the lens exits from the lens delivery passageway as well as to manipulate the injected lens within the intraocular implant site.

To use an assembled apparatus according to the present invention, a retaining clip on the plunger is removed to allow the plunger to move relative to the lens injecting body. The plunger, and specifically the plunger tip is then advanced into engagement with the deformed intraocular lens within the lens receiver. Further advancement of the plunger moves the lens into the nozzle portion of the apparatus. The nozzle tip portion and extending portion are then inserted into the eye and the plunger is advanced further to move the lens out of the nozzle tip portion into the eye. Once within the eye, the plunger tip and nozzle tip portion may be used to further manipulate the lens into proper implanted position.

BRIEF DESCRIPTION OF THE DRAWINGS

FIG. 1 shows a side view of an apparatus according to the present invention.

FIG. 1A shows a planar view of an apparatus according to the present invention.

FIG. 2 shows a planar view of a lens injecting body according to the present invention.

FIG. 3 shows a side view of the lens injecting body shown in FIG. 2.

FIG. 3A shows an end view of the lens injecting body shown in FIG. 2

FIG. 4 shows an end view of the lens injecting body shown in FIG. 2.

FIG. 5 shows a partially exploded view of the lens injecting body shown in FIG. 2.

FIG. 6 shows an end view of an extension portion according to the present invention.

FIG. 7 shows an end view of a lens receiver according to the present invention.

FIG. 8 shows an end view of a lens receiver according to the present invention.

FIG. 9 shows a side view of a cap according to the present invention.

FIG. 10 shows a cross-sectional view of the cap shown in FIG. 9.

FIG. 11 shows another cross-sectional view of the cap shown in FIG. 9

FIG. 12 shows an end view of the cap shown in FIG. 9.

FIG. 13 shows another end view of the cap shown in FIG. 9.

FIG. 14 shows another end view of the cap shown in FIG. 9.

FIG. 15 shows a top view of a nozzle portion according to the present invention.

FIG. 16 shows a side view of the nozzle portion shown in FIG. 15.

FIG. 17 shows an end view of the nozzle portion shown in FIG. 15.

FIG. 18 shows an end view of the nozzle portion shown in FIG. 15.

FIG. 19 shows a partial cross-sectional side view of the nozzle portion shown in FIG. 15.

FIG. 20 shows an end view of the nozzle portion shown in FIG. 15.

FIG. 21 shows an end view of the nozzle portion shown in FIG. 15.

FIG. 22 shows a side view of a plunger according to the present invention.

FIG. 23 shows another side view of the plunger shown in FIG. 22.

FIG. 24 shows a partial view of the plunger shown in FIG. 22.

FIG. 25 shows a partial cross-sectional view of the plunger shown in FIG. 22.

FIG. 26 shows an end view of the plunger shown in FIG. 22.

FIG. 27 shows a partial cross-sectional view of the plunger shown in FIG. 22.

FIG. 28 shows a partial view of the plunger shown in FIG. 22.

FIG. 29 shows a partial cross-sectional view of the plunger shown in FIG. 22.

FIG. 30 shows a partial cross-sectional view of the plunger shown in FIG. 22.

FIG. 31 shows a partial. cross-sectional view of a preferred embodiment of a deformable lens injecting apparatus according to the present invention.

FIG. 32 shows a side view of a lens injecting body of the apparatus shown in FIG. 31.

FIG. 38 shows a side view of a shield portion connected to the lens receiver shown in FIG. 33.

FIG. 39 shows an end view of the shield portion shown in FIG. 36.

FIG. 40 shows a bottom view of the shield portion shown in FIG. 36.

FIG. 41 shows a side view of a seated container of hydrating solution containing a lens receiver according to the present invention.

FIG. 42 shows a bottom view of the sealed container shown in FIG. 39.

FIG. 43 shows a side view of a distal portion of the sealed container shown in FIG. 41 with a distal end of the lens injecting body of FIG. 32 inserted therein.

FIG. 44 shows a side view of the distal end of the lens injecting body shown in FIG. 32 connected to the proximal end of the lens receiver shown in FIG. 33.

FIG. 45 shows an end view of the lens receiver shown in FIG. 33 with the shield shown in FIG. 38 connected hereto.

FIG. 49 shows a proximal end view of the nozzle portion shown in FIG. 46.

FIG. 50 shows a distal end view of the nozzle portion shown in FIG. 44.

FIG. 51 shows a distal end view of a nozzle tip portion of the nozzle portion shown in FIG. 44.

FIG. 52 shows a proximal end view of the nozzle tip portion shown in FIG. 49.

DETAILED DESCRIPTION OF THE PREFERRED EMBODIMENTS

Figure 33:
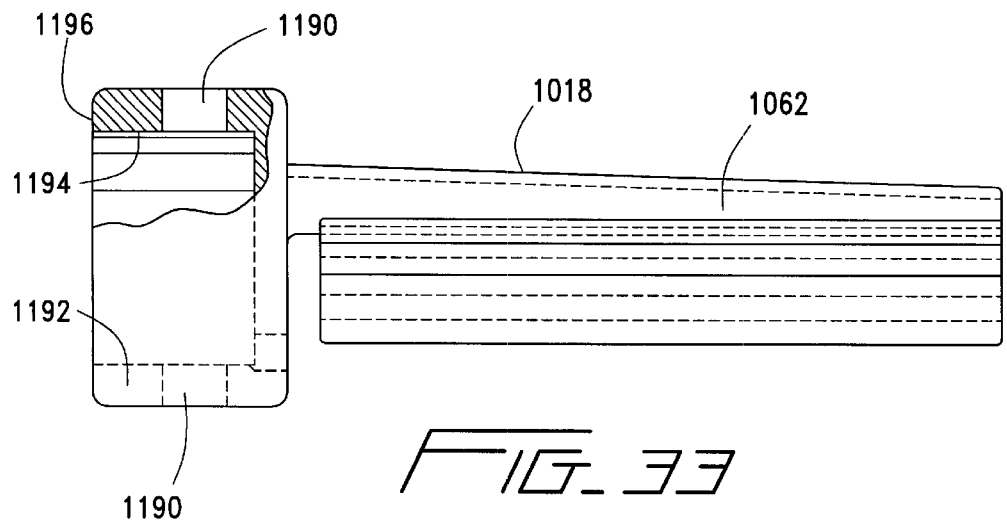
FIG. 33 shows a partial cross-sectional side view of a lens receiver of the apparatus shown in FIG. 31.

FIGS. 1–1A show a preferred embodiment of a deformable lens injecting apparatus 14 for inserting a deformable intraocular lens through a small incision into an eye. Apparatus 14 includes generally, a lens injecting body 16 including a lens receiver 18, a nozzle portion 22 connected to the lens receiver 18 and a plunger slidably disposed relative to a lens delivery passageway 26 defined by the nozzle portion 22 and lens receiver 18.

The lens injecting body 16 of apparatus 14 shown in FIG. 1 is preferably an elongated hollow translucent member made of polyethylene having a proximal end 32 and a distal end 34 as shown in FIG. 2. The transverse cross-sectional profile of lens injecting body 16 includes a major axis 46 and a minor axis 48 as shown in FIG. 3. The exterior surface of lens injecting body 16 defines a proximal finger rest portion 36 as shown in FIGS. 2–4, and a distal tapering portion 38 which transitions to a proximal endplate 42. Endplate 42 includes a pair of outwardly extending tabs 44. Finger rest portion 36, distal tapering portion 38, endplate 42 and extending tabs 44 each define longitudinal axes which are parallel with the major axis 46 of the transverse cross-sectional profile of lens injecting body 16.

As shown in FIGS. 2–5, the interior surface of lens injecting body 16 defines a proximal entrance port 52 and a distal tapering portion 54 which transitions into a lens delivery passageway 56 having an exit 58 on the distal face of endplate 34.

Lens receiver 18 is attached to the distal face of endplate 34 as shown in FIGS. 2, 3 and 5. In the preferred embodiment shown, lens receiver 18 and lens injecting body 16 are manufactured as a one-piece assembly.

Lens receiver 18 includes a first portion defining a base portion 62 and second and third portions which define a first extension portion 64 and a second extension portion 66, respectively, as shown in FIG. 2. A first live hinge 72 between base portion 62 and first extension portion 64 allows first extension portion 64 to rotate about a first longitudinal axis relative to base portion 62. A second live hinge 74 between base portion 62 and second extension portion 66 allows second extension portion 66 to rotate about a second longitudinal axis relative to base portion 62. Preferably, first live hinge 72 and second live hinge 74 are parallel and equidistant from a longitudinal axis of lens delivery passageway 26.

In FIG. 3, first extension portion 64 and second extension portion 66 are shown substantially coplanar with base portion 62 and lens receiver 18 is said to be in an open configuration. Note that lens receiver 18 defines a platform 68 when in an open configuration. First and second extension portions, 64 and 66, respectively may be operated, i.e. rotated, to what is said to be a closed configuration, as shown in FIG. 3A. When lens receiver 18 is in a closed configuration the interior surfaces of base portion 62, first extension portion 64 and second extension portion 66, define a portion of lens delivery passageway 26. Preferably, first and second extension portions cooperate to snap lock together when lens receiver 18 is in a closed configuration.

Platform 68 of apparatus 14 is preferably configured to receive a deformable intraocular lens (not shown) in a non-deformed condition. First extension portion 64 includes a first edge gripping portion 82 and second extension portion 66 includes a second edge gripping portion 84. First and second edge gripping portions 82 and 84, respectively, serve to maintain the lens in proper position within platform 68. Note from FIG. 8 that platform 68 defines a tray portion 76 for receiving an optic portion of a deformable intraocular lens and preventing the same from contacting the surface of platform 68 during storage of an intraocular lens therein.

Apparatus 14 is preferably provided with a pre-loaded lens within lens receiver 18. As shown in FIGS. 9–14, a cap 86 is preferably provided with apparatus 14 for placement over lens receiver 18. Cap 86 is preferably configured to releasably engage lens receiver while in an open configuration, in other words, cap 86 is preferably configured to releasably engage platform 68. Cap 86 is further preferably configured to releasably engage platform 68 with a pre-loaded deformable intraocular lens provided therein in a non-deformed condition. As shown in FIGS. 10–14, the inner surface 86 of cap 86 includes a first extension portion contour 88, a base portion contour 92, and a second extension contour 94. Cap 86 is further provided with a tab 96 which frictionally contacts a surface on the distal portion of base portion 62 of lens receiver 18 to releasably engage cap 86 to lens receiver 18.

FIGS. 1 and 17–21 show nozzle portion 22 according to the present invention. Nozzle portion 22 includes a lens receiver contour portion 102 which is configured to engage lens receiver 18 when lens receiver 18 is in a closed configuration. Note that nozzle portion 22 thereby functions to ensure that lens receiver 18 is maintained in a closed configuration when nozzle portion 22 is mounted thereto. Nozzle portion includes a pair of holes 104 which engage tabs 44 of lens receiver 18 to lock nozzle portion 22 to lens receiver 18. As shown in FIGS. 8 and 17, base portion 62 of lens receiver 18 includes a web portion 96 which is engaged by a web contoured portion 98 of nozzle portion 22. Web portion 96 and web contoured portion 98 cooperate to guide the advancement of nozzle portion 22 onto lens receiver and to prevent relative rotation therebetween.

Nozzle portion 22 further includes an extending portion 106 which defines a portion of lens delivery passageway 26. Note that the portion of lens delivery passageway 26 within extending portion 106 of nozzle portion 22 communicates with that of lens receiver 18. Further note that lens delivery passageway tapers distally within nozzle portion extending portion 106 as shown in FIGS. 15, 16, 18, and 19.

Extending portion 106 of nozzle portion 22 further indicates a nozzle tip portion 108 having a first tip portion 112 and a second tip portion 114 as shown in FIGS. 15, 16, 19, 20 and 21. First tip portion 112 and second tip portion 114 are separated by opposing channels 116. Note that second tip portion 114 extends distally beyond first tip portion 112.

FIGS. 22–29 show a plunger 28 according to the present invention. Plunger 28 includes a main portion 118 having a transverse cross-sectional profile which defines a web section having sections coincident as shown in FIG. 29. The proximal end of plunger 28 includes a finger rest portion 122. Main portion 118 transitions into a mid portion 124 including a first flare portion 126, a collar portion 128 and a second flare portion 132 as shown in FIGS. 22, 25 and 28. Mid portion 124, in turn, transitions into plunger extending portion 134 which is configured for axial movement relative to lens delivery passageway 26. Extending portion 134 of plunger 28 includes a plunger tip portion 136 including a first tip portion 138 and a second tip portion 142 which define a tool, specifically, a lens control portion 144 therebetween. Note that first tip portion 138 defines a broader inner face than second tip portion 142, as shown in FIG. 28.

The preferred embodiment of apparatus 14 is preferably provided to a user partially assembled. Specifically, plunger 28 is preferably inserted within lens injecting body as shown in FIGS. 1 and 1A. Note that plunger 28 is preferably provided to the user with a removable retainer clip 146 attached to main portion 118 for preventing axial movement of plunger 28 relative to lens delivery passageway 26. Further, lens receiver 18 is preferably provided with a pre-loaded deformable intraocular lens within platform 76. Cap 86 is preferably attached to lens receiver 18 to protect lens receiver 18 and the deformable intraocular lens contained therein. To use apparatus 14, the user first removes cap 86.

Apparatus 14 of the present invention stores, deforms, and delivers a deformable intraocular lens to an eye. To use apparatus 14, a user first removes cap 86. Then, while grasping lens injecting body 16 in one hand, the user uses the thumb and forefinger of the free hand to operate lens receiver 18 from an open configuration to a closed configuration. During operation of lens receiver from an open configuration to a closed configuration the deformable intraocular lens contained therein is deformed, in other words, a cross-sectional profile of the lens is altered to enable the lens to be moved through the lens delivery passageway. Once the lens receiver 18 is in a closed configuration, nozzle portion 22 is connected to lens receiver 18 thereby creating a continuous lens delivery passageway 26 through lens receiver 18 and nozzle portion 22.

The retaining clip 146 is then removed from plunger 28 which allows plunger 28 to move axially relative to lens delivery passageway 26. The plunger is then advanced until plunger tip portion 136 engages the deformed intraocular lens within lens receiver 18. The lens control portion of the plunger tip is specifically configured to prevent damage to the lens during the lens delivery process.

Further advancement of the plunger causes the lens therein to be further deformed, i.e. compressed, and moved into that portion of lens delivery passageway within nozzle portion 22. Note that the ridges 78 shown in FIG. 6 minimize surface to surface contact between the deformed lens and the lens delivery passageway within lens receiver 18.

As the lens is moved out of nozzle tip portion 108, the forces set up as a consequence of the deformation of the lens are at least partially released while the lens is within the lens delivery passageway since first tip portion and second tip portion of the nozzle tip are configured to expand slightly outwardly. Further, since first tip portion extends distally beyond second tip portion, the lens is biased downwardly as it exits from the lens delivery passageway. Once within the eye, the lens further returns from a non-deformed state and the specially configured plunger tip portion may be used to manipulate the lens into proper implanted position.

Another preferred embodiment of the present invention is shown in FIGS. 31–52. The apparatus 1014 shown in FIG. 31 is preferably provided to surgical personnel as a package of separate components which are assembled prior to use. Preferably, a lens injecting body 1016 and a plunger 1028 are provided pre-assembled and define a component of the apparatus. A lens receiver 1018 including a preferably preloaded deformable intraocular lens and a nozzle portion 1022 define components of the apparatus and are preferably provided separately for connection to the lens injecting body 1016 and plunger 1036 assembly.

The apparatus of the present invention provides a universal and reusable platform for injecting a lens into an eye. The separate components allow for a case specific lens receiver and/or a case specific nozzle portion to be connected and used with the lens injecting body and plunger assembly. Accordingly, surgical personnel need only become proficient in the use of a single lens injecting apparatus to treat a wide variety of patients according to the present invention.

As shown in FIG. 31, plunger 1028 is preferably provided preassembled with lens injecting body 1016. The plunger 1028 of apparatus 1014 is constructed similarly to the plunger 28 of apparatus 14 shown in FIG. 22. Plunger 1028, however, provides a plunger tip portion 1136 including a first tip portion 1138 and a second tip portion 1142 separated by a longitudinal slot 1152 having a depth preferably approximately half the greatest longitudinal dimension of an intraocular lens injected with the apparatus. First and second tip portions are further provided with tapered ends 1154 and 1156, respectfully, which allow plunger tip portion 1136 to more easily engage a deformable intraocular lens in a lens delivery passageway of the apparatus. The extensive contact between lens control portion 1144 and a deformed deformable intraocular lens provides greater control of the lens as the lens is advanced through and out of the lens delivery passageway of the apparatus.

FIG. 32 shows a lens injecting body 1016, preferably, an elongated, rigid hollow body which provides an exterior surface which is easily hand held and manipulated by surgical personnel. The proximal end of lens injecting body includes a finger rest 1036 for syringe type use of the apparatus. The interior surface of the lens injecting body 1016 defines a proximal entrance port 1052 for allowing plunger 1028 to be inserted into lens injecting body 1016 and a distal tapering portion 1054 which directs plunger tip portion 1036 into a plunger guide portion 1150. Plunger guide portion 1150 forms a proximal section of a lens delivery passageway 1026 of the apparatus.

Figure 34:
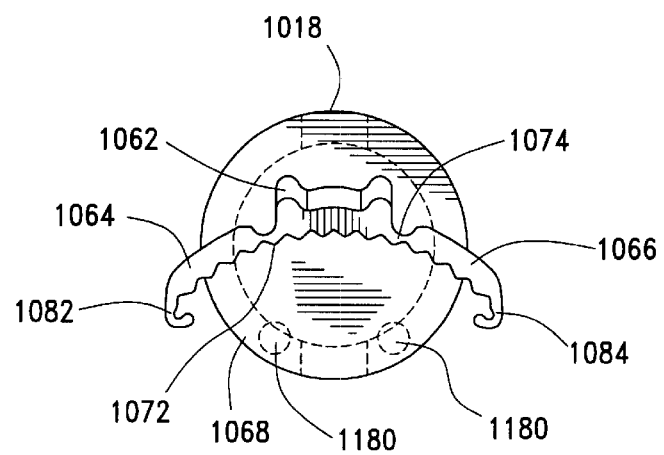
FIG. 34 shows an end view of the lens receiver shown in FIG. 33.
Figure 35:
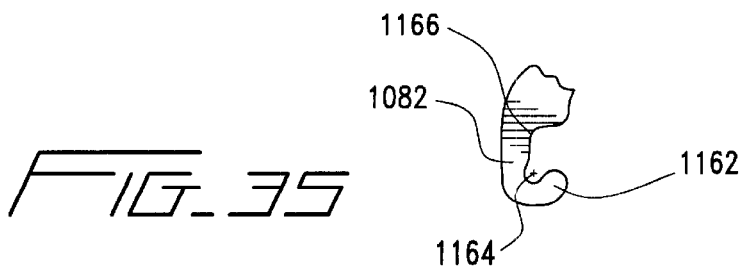
FIG. 35 shows an edge gripping portion of the extending portion of the lens receiver shown in FIG. 33.

FIGS. 33–35 show a lens receiver 1018 according to the present invention. Lens receiver 1018 is preferably provided with a preloaded deformable intraocular lens. Lens receiver 1018 stores the preloaded lens in a substantially non-deformed configuration, deforms the lens to prepare the lens for injection, stores the lens temporarily in a substantially deformed configuration prior to injection of the lens into an eye and defines a portion of a lens delivery passageway through and out of which the lens is moved by the plunger of the apparatus into the eye.

The preferred embodiment of a separate lens receiver shown in FIGS. 33–35 includes an elongated base portion 1062, and first and second extending portions 1064 and 1066, respectively, which hinge by live hinges 1072 and 1074, on either longitudinal side of base portion 1062 for operation of the lens receiver from an open configuration to a closed configuration. Lens receiver 1018 is shown in an upright position in FIG. 33 and extending portions 1064 and 1066 hinge downwardly, as further indicated in FIG. 36, to operate lens receiver 1018 from an open configuration to a closed configuration.

Figure 36:
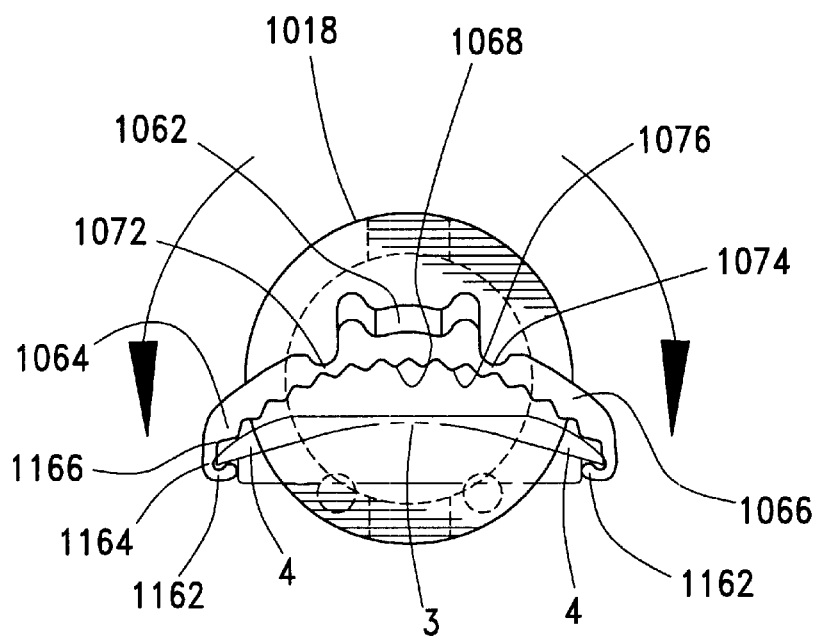
FIG. 36 shows an end view of a lens receiver of the apparatus shown in FIG. 31 with a deformable intraocular lens pre-loaded therein and being operated from an open configuration to a closed configuration.

Lens receiver 1018 is shown in an open configuration in FIGS. 33, 34, and 36. The interior surfaces of base portion 1062 and extending portions 1064 and 1066 define a platform 1068 which is configured to provide a generous loading platform for accepting a deformable intraocular lens in a non-deformed configuration as shown in FIG. 36. Pre-loading of the lens, typically an optic portion 3 surrounded by haptic portions 4, includes orienting the lens on the platform 1068 of the open lens receiver such that the optic portion 3 is received in the recessed tray portion 1076 of the base portion 1062. Pre-loading of the lens preferably further involves slightly vaulting the lens inwardly, as shown in FIG. 36 to allow each haptic portion 4 of the lens to be engaged within the first and second gripping portions 1082 and 1084, respectively, on each extending portion, as shown in FIGS. 34 and 35.

Figure 37:
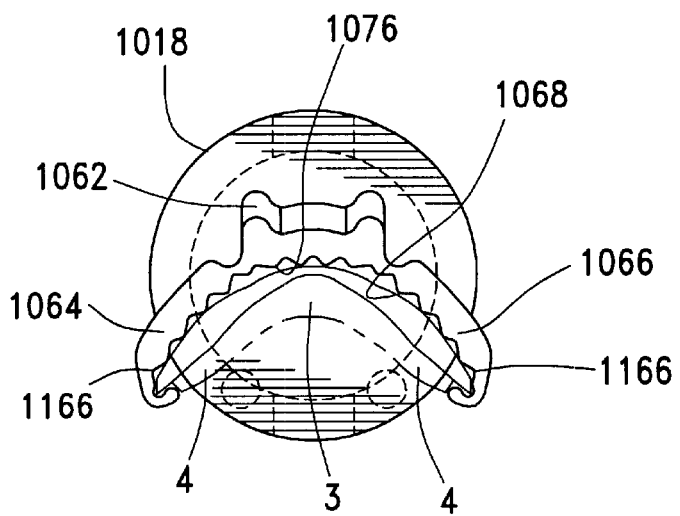
FIG. 37 shows the apparatus of FIG. 31 partially operated form an open configuration to a closed configuration.
Figure 46:
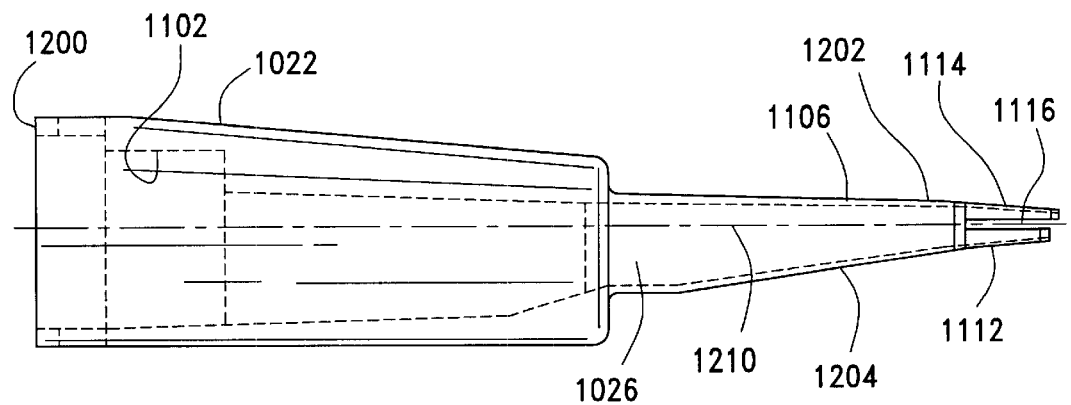
FIG. 46 shows a side view of a nozzle portion of the apparatus shown in FIG. 31 according to the present invention.

A detailed view of an edge gripping portion is shown in FIG. 35. Each edge gripping portion includes a lip portion 1162 and a haptic seat portion 1164. The haptic seat portions 1164 of each edge gripping portion 1064 and 1066 preferably transmit a slight force to the lens. The edge gripping portions thereby serve to substantially fixate the preloaded lens within the lens receiver and also to maintain a preferable slight vault in the lens as shown in FIG. 37. As will be discussed in further detail, the slight vault in the lens predisposes the lens to further deformation necessary for delivery of the lens through a small ocular incision.

Apparatus 1014 is preferably further provided with a removable shield portion 1168 which is configured to engage and maintain a preloaded lens receiver in a open configuration. A preferred shield portion 1168 is shown in FIGS. 38–40 and preferably includes a base portion 1170 including a mid-portion 1172 which defines a substantially arcuate transverse cross-sectional profile. Mid-portion 1172 serves to maintain the slightly vaulted configuration of the lens within the lens receiver as shown in FIG. 39. The base portion 1170 of shield 1168 further includes edge portions 1174 which positively engage each lip portion 1162 of the extending portions 1064 and 1066 and thereby fixate the lens receiving portion 1018 in an open configuration. As shown in FIG. 38, shield portion 1168 further includes an upwardly extending end portion 1173 which prevents distal movement of the preloaded lens in lens receiver 1018. In order to conveniently, removably, and securely connect to lens receiver 1018, as shown in FIGS. 38 and 45, shield 1168 is provided with a pair of proximally extending pins 1178 which engage a pair of holes 1180 in lens receiver 1018, as further shown in FIGS. 34 and 40. Although not shown, shield portion 1168 is further preferably configured to obstruct the advancement of plunger 1028 when connected to open lens receiver 1018, thereby providing added protection to the lens stored therein.

As shown in FIG. 41, the preloaded lens receiver 1018 with shield 1168 connected thereto is preferably stored in a sealed storage container 1182 of hydrating solution for preserving the lens during storage and transportation. As shown in FIG. 40, shield 1168 is provided with through holes 1180 for allowing hydrating solution to freely circulate to the lens while within container 1182. Container 1182 is provided with a threaded neck portion 1184 to which a threaded sealing cap 1186 is connected.

Prior to use of the apparatus, cap 1186 is removed from threaded neck 1184 which, as shown in FIG. 43, provides a port for receiving the distally extending portion 1158 of the lens injecting body 1016. Distally extending portion 1158 is provided with a set of tabs 1160 which engage holes 1190 in the proximally extending portion 1192 of lens receiver 1018 to provide a "snap-fit" connection requiring no tools or fasteners. Note that the connection occurs within container 1182. Further, note that the interior surface of proximally extending portion 1192 cooperates with the exterior surface of the distally extending portion 1158 of lens injecting body 1018 to provide a rigid connection therebetween. Specifically, and as shown in FIGS. 43 and 44, the end surface 1196 of lens receiver 1018 contacts end face 1161 of lens injecting body and the interior surface 1194 of the proximally extending portion 1192 contacts the exterior surface 1163 of lens injecting body 1016.

Once connected together, the lens injecting body 1016 and lens receiver 1018 are removed from the container as shown in FIGS. 44 and 45. Shield portion 1168 is then removed from the lens receiver allowing the stored lens to be visually inspected by surgical personnel. After satisfactory visual inspection, the lens is preferably treated with a biocompatible surgical lubricant.

The lens is then ready for further deformation in preparation for delivery to the implant site. Deformation of the lens is accomplished by the operation of lens receiver 1018 from an open configuration to a closed configuration. Specifically, and as shown in FIGS. 36 and 37, extending portions 1064 and 1066 are grasped simultaneously, preferably, by the thumb and forefinger, and hinged downwardly relative to base portion 1062.

As each extending portion of the lens receiver rotates about base portion 1162, the edge of each haptic portion rotates with each haptic seat portion 1164 of each edge gripping portion 1082. Specifically, and as shown in FIG. 35, each haptic seat portion is defined by a surface of edge gripping portion 1082 having a defined first radius of curvature.

As the extending portions progress closer to a closed configuration the haptic portions are further guided into a deformed configuration by a haptic relief portion 1166 in each edge gripping portion 1082 as shown in FIG. 35. Specifically, each haptic relief portion 1166 provides a surface against which the haptic portions may deform without causing a displacement of the haptic edge from the haptic seat portions 1164. Each haptic relief portion 1166 is defined by a surface of edge gripping portion 1082 having a defined second radius of curvature.

As the edge gripping portions 1082 and 1084 approach each other, the radius of curvature associated with the slight vault in the lens introduced to the lens during pre-loading is greatly decreased thereby causing the haptic portions of the lens to curl inwardly and ultimately to slightly overlap within the lens receiver in a "rolled" configuration (not shown).

Once actual contact is made between extending portions 1064 and 1066, the operation of lens receiver 1018 from an open configuration to a closed configuration is complete. In a closed configuration, the interior surfaces of base portion 1062 and extending portions 1064 and 1066 define a portion of the lens delivery passageway 1026 through which the lens is moved into the eye from apparatus 1014. Preferably, and as shown in FIG. 34, lens delivery passageway 1026 within closed lens receiver 1018 is provided with longitudinal ridges 1198 which greatly decrease frictional surface contact and allow for the circulation of lubricant between the interior surfaces of lens receiver 1018 and a deformed lens therein. Optional cooperating locking structure (not shown), may be provided on each extending portion 1064 and 1066 to maintain lens receiver 1018 in a closed configuration.

A preferred nozzle portion 1022 of apparatus 1014 is shown in FIGS. 46–52. Nozzle portion 1022 generally provides a portion of lens delivery passageway 1026 which communicates with the portion of lens delivery passageway within lens receiver 1018 and the intraocular implant site. Nozzle portion 1022 also serves to secure the lens receiver 1018 in a closed configuration.

Nozzle portion 1022 includes a lens receiver contour portion 1102 which is configured to engage lens receiver 1018 in a closed configuration as shown in FIGS. 31 and 46–48. Nozzle portion 1022 further includes a proximally extending portion 1200 having a set of holes 1104 for engaging a set of tabs 1044 on the endplate 1042 of lens injecting body 1016 to provide a snap-fit connection therebetween. Note that a rigid connection is provided between lens injecting body 1016 and nozzle portion 1022 in part by the extensive contact between lens receiver contour portion 1102 of nozzle portion 1022 and the exterior surface of the lens receiver 1018, as shown in FIG. 31.

Nozzle portion 1022 further includes an extending portion 1106 which defines a portion of lens delivery passageway 1026 which communicates with the portion of lens delivery passageway within lens receiver 1018 and the intraocular implant site. The lens delivery passageway tapers downwardly through extending portion 1106 and thus a lens deformed within lens receiver 1108 is further deformed by extending portion 1106 as the lens is advanced therethrough. Preferably, extending portion 1106 is configured to be substantially transparent to allow surgical personnel to visually inspect a lens advancing therethrough.

Figure 47:
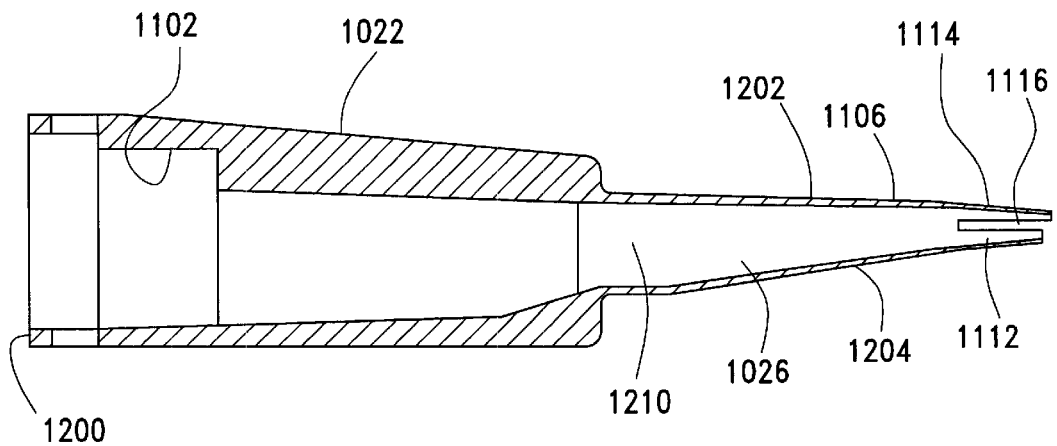
FIG. 47 shows a partial cross-sectional view of the nozzle portion shown in FIG. 46.
Figure 48:
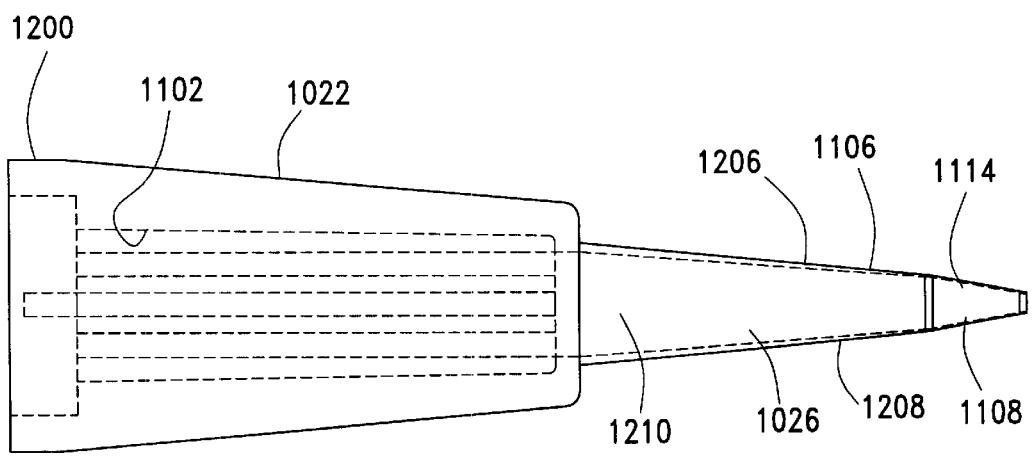
FIG. 48 shows a bottom view of the nozzle portion shown in FIG. 46.

Note that the rate at which lens delivery passageway 1026 tapers within extending portion 1106 varies along the longitudinal axis 1210 thereof Further, and as shown in FIGS. 46–47 and 49–50, the average rate at which an upper surface 1202 of lens delivery passageway approaches longitudinal axis 1210 is less than the average rate at which a bottom surface 1204 approaches axis 1210. In other words, and as can be further appreciated by referring to FIGS. 36 and 37, the optic portion of the lens which contacts the upper surface 1202 of lens delivery passageway 1026 is deformed at a lesser rate within extending portion 1106 than the haptic portions thereof As shown in FIGS. 46–48 and 51–52, nozzle portion 1022 further includes a nozzle tip portion 1108. Nozzle tip portion 1108 is configured to provide a surface which is guided into and through a small ocular incision, to allow a deformed intraocular lens advanced therethrough to release elastic energy associated with the lens deformation process in a controlled manner, to influence the direction at which a lens exits from the lens delivery passageway, and to provide a tool for manipulating the lens within the intraocular implant site. A preferred nozzle tip 1108 includes a first tip portion 1112 and a second tip portion 1114. First tip portion 1112 and second tip portion 1114 are separated by opposing longitudinal slots 1116. Further, second tip portion 1114 preferably, and as shown in FIGS. 47 and 48, extends distally beyond first tip portion 1112. Note that first and second tip portions 1112 and 1114 include channel portions 1212 and 1214 respectively. Note that channel portion 1212 is larger than channel portion 1214.

With the nozzle portion 1022 connected to the lens injecting body 1016, apparatus 1014 is fully prepared for injection of the deformed lens within lens receiver 1018 into the eye. Retaining clip 1146 is removed allowing plunger 1028, and specifically, plunger tip portion 1136 to engage the deformed intraocular lens within closed lens receiver 1018. Contact between the plunger tip portion, specifically, lens control portion 1144 and the deformed lens occurs such that plunger tip first portion is positioned above the optic portion of the lens and plunger tip second portion is positioned below the optic portions of the lens and between the haptic portions thereof Further advancement of the plunger causes the lens to be moved into the portion of lens delivery passageway 1026 within the nozzle portion extending portion 1106.

Nozzle tip portion 1108 is then inserted into the eye through a small ocular incision. Final advancement of the plunger results in expression of the lens from the nozzle tip 1108. As the lens exits from the nozzle tip portion, the first and second nozzle tip portions 1112 and 1114 yield outwardly slightly to release elastic energy from the lens. The lens may be adjusted within the implant site with the plunger tip portion 1136. Apparatus 1014 is then withdrawn from the eye to complete the injection of the lens.

What is claimed is:

1. A deformable intraocular lens injecting apparatus for inserting a deformable intraocular lens through a small incision into an eye, said apparatus comprising:

a lens injecting body;

a separate lens receiver configured to be connected to a distally extending portion of said lens injecting body and configured to be operated between an open configuration and a closed configuration;

a separate nozzle portion configured to be connected to said lens injecting body and provided with a tip portion configured to be inserted through a small ocular incision;

said nozzle portion and said lens receiver defining a lens delivery passageway; and a plunger slidably disposed relative to said lens delivery passageway and configured to engage a deformable intraocular lens within said lens delivery passageway of said lens receiver, and to move said deformable intraocular lens out of said lens delivery passageway into said eye, wherein a proximally extending portion of said lens receiver is provided with a pair of holes for engaging a pair of tabs provided on said lens injecting body for connecting said lens receiver to said lens injecting body.

2. A deformable intraocular lens injecting apparatus according to claim 1 wherein said lens receiver is configured to store a lens in a slightly vaulted configuration.

3. A deformable intraocular lens injecting apparatus according to claim 2, wherein said lens receiver is preloaded and stored within a container at least partially filled with saline solution, said container being provided with a threaded neck to which a threaded cap is connected.

4. A deformable intraocular lens injecting apparatus according to claim 3, wherein said container is configured to receive a distal end of said lens injecting body for connection of said lens receiver to said distal end of said lens injecting body within said container.

5. A deformable intraocular lens injecting apparatus according to claim 4 wherein operation of said lens receiver from an open configuration to a closed configuration deforms a deformable intraocular lens.

6. A deformable intraocular lens injecting apparatus according to claim 5, wherein said lens receiver includes a first hinged extending portion, and a second hinged extending portion, said first and second hinged extending portions being configured to hinge relative to a base portion for operating said lens receiver from an open configuration to a closed configuration.

7. A deformable intraocular lens injecting apparatus according to claim 6, said apparatus being configured such that when said apparatus is held in a longitudinally horizontal and upright position said first extending portion and said second extending portion hinge downwardly to operate said lens receiver from an open configuration to a closed configuration.

8. A deformable intraocular lens injecting apparatus according to claim 7, wherein said first and second extending portions are each provided with a lens edge gripping portion.

9. A deformable intraocular lens injecting apparatus according to claim 8, wherein each lens edge gripping portion includes a haptic seat portion and a haptic relief portion.

10. A deformable intraocular lens injecting apparatus according to claim 6, wherein said lens receiver is provided with a removably connected shield portion.

11. A deformable intraocular lens injecting apparatus according to claim 10, wherein said shield portion is configured for maintaining said lens receiver in an open configuration.

12. A deformable intraocular lens injecting apparatus according to claim 11, wherein said shield portion is configured for preventing advancement of said plunger tip relative to said lens receiver.

13. A deformable intraocular lens injecting apparatus according to claim 12, wherein said shield portion includes a base portion, edge portions, a distal end portion, and a pair of proximally extending pins for engaging a corresponding set of holes in said lens receiver.

14. A deformable intraocular lens injecting apparatus according to claim 13, wherein said base portion of said shield includes a transverse arcuate section for maintaining a vaulted configuration of a lens stored in said lens receiver.

15. A deformable intraocular lens injecting apparatus according to claim 6, wherein said nozzle portion is provided with a lens receiver contour portion for engaging said lens receiver in a closed configuration.

16. A deformable intraocular lens injecting apparatus according to claim 15, wherein an upper surface of said lens delivery passageway within said nozzle portion tapers towards a longitudinal axis of said nozzle portion at a first rate and a lower surface of said lens delivery passageway tapers towards said longitudinal axis of said nozzle portion at a second rate different from said first rate.

17. A deformable intraocular lens injecting apparatus according to claim 1, wherein at least a portion of said lens delivery passageway is provided with longitudinal ridges.

18. A deformable intraocular lens injecting apparatus according to claim 1, wherein said plunger includes a tip portion, said tip portion includes a longitudinal slot at least half as long as a greatest longitudinal dimension of a deformable intraocular lens injected with said apparatus.

19. A method of preparing a deformable intraocular lens for injection into the eye of a patient including the steps of:

providing a lens receiver with a pre-loaded deformable intraocular lens in a container;

inserting a portion of a lens injecting body into said container and connecting said lens receiver to said lens injecting body in said container; and, removing said lens injecting body with said lens receiver connected thereto from said container.

20. A method according to claim 19, further including the step of:

operating said lens receiver from an open configuration to a closed configuration to deform said pre-loaded deformable intraocular lens from a substantially non-deformed configuration to a deformed configuration.

* * * * *